(12) United States Patent
Shalaby et al.

(10) Patent No.: US 8,383,140 B2
(45) Date of Patent: Feb. 26, 2013

(54) ABSORBABLE CRYSTALLINE COPOLYESTER-BASED BIOACTIVE HYDROFORMING LUMINAL LINER COMPOSITIONS

(75) Inventors: Shalaby W Shalaby, Anderson, SC (US); Kenneth David Gray, Clemson, SC (US); Georgios T Hilas, Anderson, SC (US)

(73) Assignee: Poly-Med, Inc., Anderson, SC (US)

( * ) Notice: Subject to any disclaimer, the term of this patent is extended or adjusted under 35 U.S.C. 154(b) by 292 days.

(21) Appl. No.: 12/798,457

(22) Filed: Apr. 5, 2010

(65) Prior Publication Data

US 2010/0256081 A1 Oct. 7, 2010

Related U.S. Application Data

(60) Provisional application No. 61/211,871, filed on Apr. 3, 2009.

(51) Int. Cl.
*A01N 25/34* (2006.01)
(52) U.S. Cl. .................................................. 424/412
(58) Field of Classification Search ................. None
See application file for complete search history.

(56) References Cited

U.S. PATENT DOCUMENTS

| | | |
|---|---|---|
| 4,938,763 A | 7/1990 | Dunn et al. |
| 5,612,052 A | 3/1997 | Shalaby |
| 5,714,159 A | 2/1998 | Shalaby |

*Primary Examiner* — Carlos Azpuru
(74) *Attorney, Agent, or Firm* — McCormick, Paulding & Huber LLP

(57) ABSTRACT

Bioactive, hydroforming luminal liner compositions are formed of high molecular weight crystalline, absorbable copolyesters dissolved in a liquid derivative of a polyether glycol that undergoes transformation into a tissue-adhering, resilient interior cover or liner for the controlled release of its bioactive payload at clinically compromised conduits in humans as in the case of bacteria- and yeast-infected vaginal canals, esophagi, and arteries following angioplasty.

4 Claims, No Drawings

ABSORBABLE CRYSTALLINE COPOLYESTER-BASED BIOACTIVE HYDROFORMING LUMINAL LINER COMPOSITIONS

The present application claims the benefit of prior provisional application, U.S. Ser. No. 61/211,871, filed Apr. 3, 2009.

FIELD OF THE INVENTION

The present invention is directed to bioactive, absorbable, crystalline copolyester-based hydroforming luminal liner compositions for producing a resilient, adhering liner onto the lumens of specific body conduits in order to treat or prevent undesirable clinical events through the controlled release of at least one bioactive agent contained therein, such as for treating vaginal and esophageal yeast infections and preventing restenosis following arterial angioplasty.

BACKGROUND OF THE INVENTION

Liquid formulations of amorphous solid and viscous liquid copolyesters, which undergo precipitation or hydrogel formations in aqueous media, respectively, have been described in the prior art as carriers for the controlled release of bioactive agents. These entailed (a) solutions of essentially amorphous lactide/glycolide copolymers in liquid cyclic compounds, such as N-methyl pyrrolidone (U.S. Pat. No. 4,938,763); and (2) viscous liquids of polyether-esters with or without the incorporation of lower viscosity liquid diluents comprising lower molecular weight polyether-ester (U.S. Pat. Nos. 5,612,052 and 5,714,159). However, the solid polyester-based composition of U.S. Pat. No. 4,938,763 required the use of a cyclic tissue-irritating solvent and the low molecular weight of the polymers did not support the formation of resilient, adhering films or mechanically compatible luminal liners, that are defined as a continuous internal cover for biological conduits. Meanwhile, the hydrogel-forming compositions of U.S. Pat. Nos. 5,612,052 and 5,714,159 were not designed to a yield resilient, tissue-adhering, mechanically compatible luminal liner but rather gel-like materials. This provided an incentive to pursue the study, subject of the present invention, which is directed to the use of special solutions of crystalline, high molecular weight copolyesters mixed with non-reactive liquid polymers as carriers of bioactive agents, which, upon application onto the luminal surface of biological conduits, transform in the presence of water (hydroform) into a tissue-adhering, cohesive, resilient internal cover or liner that is capable of the controlled release of its bioactive payload as required for treating the application sites. Shortly after the release of the bioactive agents, the liner degrades to compliant microlamella.

SUMMARY OF THE INVENTION

The present invention is directed to a bioactive, absorbable, hydroforming luminal liner composition comprising at least one crystalline copolyester having a heat of fusion of at least 10 J/g, preferably at least 20 J/g, most preferably at least 30 J/g, and a molecular weight in excess of 20 kDa, preferably in excess of 35 kDa, most preferably in excess of 50 kDa, at least one liquid derivative of a polyether glycol and at least one bioactive agent selected from the group consisting of antimicrobial, antiviral, antiretroviral, anti-inflammatory, antiproliferative, antineoplastic, immunosuppressing, and anesthetic agents, wherein the at least one crystalline copolyester is selected from the group consisting of linear segmented polyether-esters, segmented polyaxial copolyester and polyaxial polycarbonate-esters, and wherein the at least one liquid derivative of a polyether glycol is selected from the group consisting of acylated polyethylene glycol, benzylated polyethylene glycol, o-alkylated polyethylene glycol, o-benzylated polyethylene glycol, acylated copolymers of ethylene and propylene oxide, benzylated copolymer of ethylene and propylene oxide and benzylated copolymer of ethylene and propylene oxide.

A clinically important aspect of this invention deals with a bioactive, hydroforming luminal liner composition comprising at least one absorbable, crystalline copolyester having a heat of fusion of at least 10 J/g, preferably at least 20 J/g, most preferably at least 30 J/g, and a molecular weight in excess of 20 kDa, preferably in excess of 35 kDa, most preferably in excess of 50 kDa, at least one liquid derivative of a polyether glycol and at least one bioactive agent selected from the group consisting of antimicrobial, antiviral, antiretroviral, anti-inflammatory (steroidal and non-steroidal), antiproliferative, antineoplastic, immunosuppressing, and anesthetic agents, wherein the at least one bioactive agent is (a) an antifungal agent selected from the group consisting of ketoconazole, terbinafine, miconazole, voriconazole, and fluconazole as part of an antifungal formulation for treating vaginal, esophageal or nail fungal infections in humans and animals; (b) an antibacterial agent selected from the group consisting of metronidazole, clindamycin, doxycycline, and tobramycin as part of a formulation for treating vaginal or esophageal bacterial infections in human and animals; and (c) antibiotic agents selected from the group consisting of polymyxin B, triclosan, clindamycin, cephalexin, dicloxacillin, gentamicin, vancomycin, and ciprofloxacin. The polymers, subject of the instant invention, can be used as carriers for (a) treating steroid-responsive dermatitis using, for example, hydrocortisone or triamcinolone; and (b) septic arthritis and osteomyelitis using vancomycin or methylprednisolone. Meanwhile, the successful use of these formulations requires an applicator kit for delivering the active formulation comprising a solid applicator in a tubular housing of slightly larger diameter wherein the applicator has clockwise, helical grooves 2 mm in width and depth, both the applicator and tubular housing are threaded at their ends to allow secure assembling of the kit. General methods of preparation, sterilization, and packaging entail the steps of a) dissolving the crystalline copolyester in the liquid derivative of a polyether glycol;
b) heat-sterilizing the liquid solution;
c) mixing the sterilized liquid solution with the antifungal or antibacterial agent, under aseptic conditions;
d) transferring an aliquot of active formulation from step "c" to a pre-sterilized plastic tubular housing of the applicator and securing the applicator in the housing;
e) placing the assembled applicator kit from step "d" in a sealable clear plastic pouch;
f) heat-sealing the plastic pouch from step "e."

Additionally, a method for application of said antifungal formulation onto the mucosal lining of the vagina of a human or animal entails the steps of:

a) removing the applicator loaded with the liquid drug-loaded formulation;
b) inserting the applicator into the vaginal canal using a clockwise, inward movement; and
c) removing the applicator from the vaginal canal using a counter-clockwise, outward movement.

Another clinically important aspect of the instant invention deals with a bioactive, absorbable, hydroforming luminal liner composition comprising at least one absorbable, crystalline copolyester having a heat of fusion of at least 10 J/g, preferably at least 20 J/g, most preferably at least 30 J/g, and a molecular weight in excess of 20 kDa, preferably in excess of 35 kDa, most preferably in excess of 50 kDa, at least one liquid derivative of a polyether glycol and at least one bioactive agent selected from the group consisting of antimicrobial, antiviral, antiretroviral, anti-inflammatory, antiproliferative, antineoplastic, immunosuppressing, and anesthetic agents, wherein the at least one bioactive agent is one or two agents capable of preventing restenosis following arterial angioplasty, and wherein preventing restenosis is effected by a combination of an anti-inflammatory agent and a second agent selected from the group consisting of antiproliferative, antineoplastic, immunosuppressing, and antimicrobial agents and further wherein the anti-inflammatory agent is naproxen, the antineoplastic agent is paclitaxel or curcumin and the immunosuppressing agent is rapamycin. Meanwhile, the successful use of the formulation requires an applicator kit, similar to those used in endovascular stent deployment, for delivering the active formulation comprising an inflatable inner catheter inside a blind catheter with multiple holes in the axial wall for the extrusion of the liquid formulation onto the luminal wall upon inflating the inner catheter. General methods of preparation, sterilization, and packaging the catheter components of the applicator kit, entail the steps of:

a) dissolving the crystalline polyester in the liquid derivative of a polyether glycol;
b) heat-sterilizing the liquid solution;
c) mixing the sterilized liquid solution with the bioactive agent or agents under aseptic conditions;
d) transferring an aliquot of the active formulation from step "c" into the blind end of the outside catheter;
e) inserting the inflatable inner catheter inside the outer one up to the point preceding the holed zone of the blind catheter; and
f) incorporating the two-catheter kit into a modified deployment kit for endovascular stents.

DETAILED DESCRIPTION OF PREFERRED EMBODIMENTS

From a clinical perspective, the present invention in a major aspect is concerned with the treatment of vaginal and esophageal candidiasis. Vaginal Candidiasis (VC) is a common medical problem in women and is associated with discomfort, particularly due to a copious discharge, which is often accompanied by odor. Currently available treatments of yeast infection include (1) a systemic oral administration therapy; (2) use of topical creams; and (3) use of intravaginal suppositories which release the drug after melting or dissolving in the vagina. However, the systemic administration can lead to drug toxicity, while all other currently used forms for intravaginal administration are subject to uncontrolled leakage of the drug during the vaginal discharge, creating unsanitary conditions and discomfort while resulting in unpredictable bioavailability of the drug. Esophageal candidiasis (EC) is another form of fungal infection caused in most cases by a *candida* species and results in sore throat and difficulty in swallowing. This infection is becoming more serious with the growing number of HIV patients who are highly susceptible to yeast infection. The orally administered treatment options of EC using oral formulations are particularly effective in HIV patients. However, there have been concerns about the clinical relapse in these patients, which is dependent upon the degree of immunosuppression apart from the potential hepatotoxicity associated with high or prolonged doses of orally administered drugs. Clinical shortcomings of the current treatments of VC and EC evoked the need to explore the development of topically administered drug delivery systems that are not affected by the aqueous vaginal discharge in the vagina and food transport in the esophagus, in part because of its good adhesion to the vaginal and esophageal linings to provide predictably modulated release of the drug. The need for such a novel drug delivery system prompted the pursuit of the study, subject of the present invention.

Compositions of the instant invention are designed to (1) be injectable or extrudable liquid formulations that contain a crystalline absorbable copolyester dissolved in a water-soluble liquid polyalkylene glycol with ester or ether end-groups—this is to avoid reactions (causing reduction in molecular weight) with the crystalline copolyester during storage and hence, providing needed shelf-life stability; (2) be liquid formulations having at least one bioactive agent solubilized or microdispersed therein so as to provide the desired release profile when the formulations are applied to the biological sites to form flexible covers or liners on the wall of the application sites, which are typically conduits such as vaginal canals, esophagi, and blood vessels; (3) be formulations as described in item 1 which are capable of transforming into tissue adhering, resilient crystalline covers or liners—the transformation of the liquid to a resilient crystalline film, cover, or liner is achieved through the migration of the water-soluble liquid polyalkylene glycol derivative to the aqueous environment causing the crystalline polyester to hydroform (undergo phase transition in the presence of water) or simply to undergo phase transition to a crystalline film or liner; (4) undergo phase transition in the presence of water (hydroforming) into crystalline film or liner that adheres well to the surface of the luminal wall by virtue of having flexible polar polyester segments and preferably hydrophilic segments in the polymer chain as well—the hydrophilic and polar flexible segments provide adequate adhesion to the biological lining and low frictional resistance towards adjacent fluids so as to prevent dislocation or migration of the liner from the application site in the presence of shear stresses caused by movement of biological fluids at the application site; (5) form in a timely manner a thin film or liner on the luminal wall that resists dislocation and migration from the application site—the thickness of the film or liner can be controlled by varying the composition and/or thickness of the precursors liquid formulation which allows the modulation of the drug release profile; and (6) allow their use as carriers and precursors of liners that permit incorporating a broad range of bioactive agents without causing any drug-polymer chemical interaction—the bioactive agents include, among several types of drugs, those used for treating different forms of vaginal and esophageal infections (e.g., bacterial, yeast, and viral), those capable of preventing vascular restenosis following angioplasty (e.g., immunosuppressing, antineoplastic, and anti-inflammatory agents), and those used for treating periodontitis (e.g., antibacterial agents).

Depending upon the site of the application, the present invention provides applicator kits capable of delivering, uniformly, an aliquot of the liquid formulation at the application site that undergoes a timely transformation (hydroformation) to a crystalline, drug-releasing film or liner at the site.

Further illustrations of the present invention are provided by the following examples:

EXAMPLE 1

Synthesis of a Typical Absorbable Crystalline Copolyester, P-1

The polymer was prepared using the general procedure for the synthesis of crystalline, segmented, polyaxial copolyesters of U.S. Pat. No. 7,348,364 and U.S. patent application Ser. No. 11/598,427, both of which are incorporated herein by reference. An amorphous polymeric initiator comprising 35/14/9 (molar) c-caprolactone/trimethylene carbonate/glycolide was made and end-grafted to form the crystalline end-grafts comprising 42/2 (molar) l-lactide/glycolide to yield a copolyester made of 35/14/34/17 (molar) caprolactone/trimethylene carbonate/l-lactide/glycolide. The polymer was characterized for identity (IR, NMR), molecular weight (in terms of inherent viscosity), and thermal property (DSC). It was shown to have an inherent viscosity of 1.45 dL/g, melting temperature of 109° C., and heat of fusion of 7.4 J/g.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims. Moreover, Applicant hereby discloses all subranges of all ranges disclosed herein. These subranges are also useful in carrying out the present invention.

What is claimed is:

1. A bioactive, hydroforming, luminal liner composition comprising
    at least one crystalline, absorbable copolyester having a heat of fusion of at least 10 J/g and a molecular weight of greater than of 20 kDa;
    at least one liquid derivative of a polyether glycol;
    and at least one bioactive agent selected from the group consisting of antimicrobial, antiviral, antiretroviral, anti-inflammatory, antiproliferative, antineoplastic, immunosuppressing, and anesthetic agents.

2. A bioactive, hydroforming luminal liner composition as in claim 1 wherein the at least one crystalline, absorbable copolyester is selected from the group consisting of linear segmented polyether-esters, segmented polyaxial copolyesters and polyaxial polycarbonate-esters.

3. A bioactive, hydroforming luminal liner composition as in claim 1 wherein the at least one liquid derivative of a polyether glycol is selected from the group consisting of acylated polyethylene glycol, benzylated polyethylene glycol, o-alkylated polyethylene glycol, o-benzylated polyethylene glycol, acylated copolymers of ethylene and propylene oxide, benzylated copolymers of ethylene and propylene oxide and benzylated copolymers of ethylene and propylene oxide.

4. A bioactive, absorbable, hydroforming luminal liner composition as in claim 3 further comprising a method of preparation, sterilization, and packaging entailing the steps of:
    a) dissolving the crystalline copolyester in the liquid derivative of a polyether glycol;
    b) heat-sterilizing the liquid solution;
    c) mixing the sterilized liquid solution with the antifungal agent, under aseptic conditions;
    d) transferring an aliquot of active formulation from step "c" to a pre-sterilized plastic tubular housing of an applicator and securing the applicator in a housing;
    e) placing the assembled applicator kit from step "d" in a sealable clear plastic pouch;
    f) heat-sealing the plastic pouch from step "e."

* * * * *